(12) United States Patent
Kleppe et al.

(10) Patent No.: US 10,048,481 B2
(45) Date of Patent: Aug. 14, 2018

(54) SCANNING MICROSCOPE AND METHOD FOR DETERMINING THE POINT SPREAD FUNCTION (PSF) OF A SCANNING MICROSCOPE

(71) Applicant: Carl Zeiss Microscopy GmbH, Jena (DE)

(72) Inventors: Ingo Kleppe, Jena (DE); Yauheni Novikau, Jena (DE); Ralf Netz, Jena (DE); Michael Kieweg, Berlin (DE); Christoph Nieten, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 58 days.

(21) Appl. No.: 15/029,361

(22) PCT Filed: Oct. 10, 2014

(86) PCT No.: PCT/EP2014/071776
§ 371 (c)(1),
(2) Date: Apr. 14, 2016

(87) PCT Pub. No.: WO2015/055534
PCT Pub. Date: Apr. 23, 2015

(65) Prior Publication Data
US 2016/0267658 A1 Sep. 15, 2016

(30) Foreign Application Priority Data
Oct. 15, 2013 (DE) .................. 10 2013 017 124

(51) Int. Cl.
| G02B 21/06 | (2006.01) |
| G06T 5/00 | (2006.01) |
| G06T 5/50 | (2006.01) |
| G01N 21/64 | (2006.01) |
| G02B 21/00 | (2006.01) |
| G02B 27/58 | (2006.01) |
| G06T 7/00 | (2017.01) |

(52) U.S. Cl.
CPC ......... *G02B 21/06* (2013.01); *G01N 21/6458* (2013.01); *G02B 21/008* (2013.01); *G02B 21/0072* (2013.01); *G02B 21/0076* (2013.01); *G02B 27/58* (2013.01); *G06T 5/003* (2013.01); *G06T 5/50* (2013.01); *G06T 7/97* (2017.01); *G06T 2207/10056* (2013.01); *G06T 2207/10064* (2013.01); *G06T 2207/10152* (2013.01)

(58) Field of Classification Search
None
See application file for complete search history.

(56) References Cited

U.S. PATENT DOCUMENTS

| 9,445,003 | B1* | 9/2016 | Lelescu | H04N 5/23232 |
| 9,671,600 | B2* | 6/2017 | Bathe | |
| 2002/0171825 | A1* | 11/2002 | Krantz | G01J 3/508 |
| | | | | 356/138 |
| 2003/0076571 | A1* | 4/2003 | MacAulay | G02B 21/0028 |
| | | | | 359/237 |
| 2005/0057744 | A1* | 3/2005 | Pohle | G01S 7/4813 |
| | | | | 356/139.03 |
| 2009/0242801 | A1* | 10/2009 | Engelhardt | G01N 21/6428 |
| | | | | 250/459.1 |

(Continued)

FOREIGN PATENT DOCUMENTS

| DE | 10 2011 114 500 A1 | 4/2013 |
| DE | 20 2011 114 500 A1 | 4/2013 |

OTHER PUBLICATIONS

P. Pankajakshan, B. Zhang, L. Blanc-Feraud, Z. Kam, J. C. Olivo-Marin and J. Zerubia, "Parametric Blind Deconvolution for Confocal Laser Scanning Microscopy," 2007 29th Annual International Conference of the IEEE Engineering in Medicine and Biology Society, Lyon, 2007, pp. 6531-6534.*

(Continued)

*Primary Examiner* — Kim Vu
*Assistant Examiner* — Nathan Bloom
(74) *Attorney, Agent, or Firm* — Duane Morris LLP

(57) ABSTRACT

A method for operating a scanning microscope and for determining point spread functions, with which sample images are recorded with the scanning microscope. The method includes scanning a sample with at least one illuminating light beam; recording at least one sample image with a detector device during a scan by the illuminating light beam; and comprising the point spread function, with which a sample image is recorded, from the at least one sample image. A detector device having receiving elements is used, where the distance between the receiving elements is smaller than a diffraction disk that generates a sample point on the detector device. Detector signals, generated by means of the receiving elements, are read out for each of the different positions of the illuminating light beam on the sample, as a result of which the scanning of the sample allows the detector signals, which are read out, to generate a plurality of sample images. In this case the point spread functions with respect to the different detector signals are defined in each instance by means of an illumination point spread function and a detection point spread function. With respect to all of the detector signals, a matching illumination point spread function is assumed that is shifted in accordance with the scanning motion for different detector signals. In addition, with respect to all of the detector signals, a matching detection point spread function is assumed that takes account of a spatial offset between the detector elements. The plurality of sample images are used to compute the illumination point spread function and the detection point spread function, and these functions are used to compute the point spread functions with respect to the different detector signals. In addition, the invention also relates to a corresponding scanning microscope.

15 Claims, No Drawings

(56) References Cited

U.S. PATENT DOCUMENTS

| | | | |
|---|---|---|---|
| 2010/0034429 A1* | 2/2010 | Drouin | G06T 7/521 382/108 |
| 2010/0296749 A1* | 11/2010 | Kikuchi | G06T 5/003 382/255 |
| 2010/0329582 A1 | 12/2010 | Albu et al. | |
| 2014/0313576 A1* | 10/2014 | Uhl | G02B 21/14 359/385 |
| 2015/0294186 A1* | 10/2015 | Ali | G06K 9/40 382/199 |
| 2015/0378141 A1* | 12/2015 | Bathe | G02B 21/0044 359/385 |
| 2016/0062100 A1* | 3/2016 | Cohen | G02B 21/0056 348/79 |
| 2017/0192216 A1* | 7/2017 | Bathe | G02B 21/0072 |

OTHER PUBLICATIONS

Praveen Pankajakshan. Thesis: Blind Deconvolution for Confocal Laser Scanning Microscopy. Signal and Image processing. Universit'e Nice Sophia Antipolis, 2009.*

Translation of WIPO searching authorities written opinion for the WO of the present application: Wo2015/055534.*

Translation of International Preliminary Report on Patentability(Chapter I of Patent Cooperation Treaty), Written Opinion of International Searching Authority dated Apr. 28, 2016.

Pankajakshan;"Parametric Blind Deconvolution for Confocal Laser Scanning Microscopy (CLSM)-Proof of Concept";http://hal.archives-ouvertes.fr/docs/0/0/27/02/92/PDF/report;1-45.

Conchello, et al.; "Parametric blind deconvolution of fluorescence microscopy images: Preliminary results"; Proceedings of SPIE, Jan. 1996; pp. 1-11.

Tao,et al;"A robust blind convolution based on estimation of point spread function parameters"; Electronic Imaging & Multimedia Technology IV, Dec. 2005;Proc of SPIE; 5637:581-589.

Kundar, Deepa, et al.; "Blind Image Deconvolution"; IEEE Signal Processing Magazine May 1996; XP-001188901; 13(3):43-64.

Amizic, Bruno, et al.; "Sparse Bayesian blind image deconvolution with parameter estimation"; EURASIP Journal on Image and Video Processing, Jan. 2012; 2012(1)1-15.

Sheppard, C.J.R., et al.; "Super-resolution in Confocal Imaging"; Optik 1988; 80(2):53-54.

Sroubek, F., et al.; "Simultaneous super-resolution and blind deconvolution"; Journal of Physics: Conference Series 2008; 124:1-8.

Schwille, Petra and Haustein Elke; "Fluorescence Correlation Spectroscopy—An Introduction to its Concepts and Applications"; Experimental Biophysics Group; pp. 1-33.

Müller, Claus B. and Enderlein, Jörg; "Image Scanning Microscopy"; Physical Review Letters 2010; 104(19):198101-1—198101-4.

Pankajakshan, Praveen, et al.; "Parametric Blind Deconvolution for Confocal Laser Scanning.Microscopy (CLSM)-Proof of Concept"; Apr. 2008; INRIA Gefunden im Internet: URL:http://hal.archives-ouvertes.fr/docs/0/0/27/02/92/PDF/report.pdf; pp. 1-45.

Conchello, Jose-Angel, et al.; "Parametric blind deconvolution of fluorescence microscopy images: Preliminary results"; Proceedings of Spie, Spie — International Society for.

Tao, Qingchuan, et al.; "A robust blind convolution based on estimation of point spread function parameters"; Electronic Imaging and Multimedia Technology Iv, Dec. 2005; Proc of Spie - XP040196955; 5637:581-589.

Kundar, Deepa, et al.; "Blind Image Deconvolution"; IEEE Signal Processing Magazine.

Amizic, Bruno, et al.; "Sparse Bayesian blind image deconvolution with parameter estimation"; Eurasip Journal on Image and Video Processing, Jan. 2012; XP055091242;.

Sroubek, F., et al.; "Simultaneous super-resolution and blind deconvolution"; Journal of.

* cited by examiner

SCANNING MICROSCOPE AND METHOD FOR DETERMINING THE POINT SPREAD FUNCTION (PSF) OF A SCANNING MICROSCOPE

RELATED APPLICATIONS

The present application is a U.S. National Stage application of International PCT Application No. PCT/EP2014/071776 filed on Oct. 10, 2014 which claims priority benefit of German Application No. DE 10 2013 017 124.5 filed on Oct. 15, 2013, the contents of each are incorporated by reference in their entirety.

FIELD OF THE INVENTION

The present invention relates, in a first aspect to a method for operating a scanning microscope and for determining point spread functions, with which sample images are recorded by the scanning microscope. In a second aspect, the invention relates to a the structure of the scanning microscope.

BACKGROUND OF THE INVENTION

An important objective in the analysis of a sample with a scanning microscope is to determine the quantitative information about the sample. This information can relate, for example, to the spatial distribution of fluorescent molecules, in particular, the number or density of fluorescent emitters.

The light intensity, emitted by fluorescent molecules or other sample structures of interest, is often measured; and this light intensity depends monotonically on the number or density of the molecules of interest. However, in this case only relative quantitative statements are easily possible with such a measurement technique. That is, a determined number or density is given in arbitrary units. Therefore, it may be expedient to carry out a quantitative comparison only with measured data from the same measurement.

In fluorescence correlation microscopy (FCS) fluctuations in the fluorescence intensities are analyzed by means of a correlation analysis. This approach allows an absolutely quantitative analysis, in which a density or concentration of substances of interest is not given in arbitrary units, but in physical quantities. However, precise knowledge of the observed sample volume is required for a reliable interpretation of the data, i.e., precise knowledge of the sample volume that contributes to a signal from a pixel of a recorded sample image.

The sample volume can be computed, if the point spread function, with which the sample analysis is performed, is known. The point spread function (PSF) is also referred to as a spatial response or blurring function.

Even in the case of other interpretation methods, knowledge of the analyzed sample volume is required to determine the absolute quantitative values, which can be done by means of the point spread function.

The point spread function depends on all of the elements in the optical path of the microscope. In principle, it is possible to compute a theoretical PSF, if the optical parameters of the elements in the beam path are known. However, the actual PSF can deviate from the theoretical PSF, for example, due to the production dependent fluctuations in the optical elements; due to the variances in the use of the elements; due to the disregarded variances in the immersion medium, which is used with respect to an immersion medium, which is used in the computation; or due to the variances in the temperature of the optical elements with respect to a temperature that is assumed in the computation.

Therefore, more accurate results can be obtained, if the PSF is determined by experiment. For this purpose, it is possible to analyze, in particular, a reference sample that comprises objects, so-called beads, that are smaller than the resolution of the scanning microscope. The full width at half maximum (FWHM) of the PSF may be regarded as the resolution.

Although the PSF for the objective lens that is used can be determined with a high degree of accuracy by such a reference measurement, said reference measurement does not take into consideration the elements, which are associated with the actual sample, for example, the immersion medium and the temperature dependence of the refractive index thereof. This temperature dependence can be high, especially with oil as the immersion medium. Moreover, any variance in the thickness of a cover glass that is used is not taken into consideration. This can lead to a spherical aberration. Any inclination of the cover glass may lead to astigmatism and coma of the PSF.

The error in a computed PSF or a PSF, determined in a reference measurement, with respect to the actual PSF for the analysis of the actual sample may be large, in particular, in the vertical direction. The vertical direction is supposed to denote the direction of the optical axis that runs from an objective lens to the sample. As a result, the sample volume, analyzed with a detector element, can vary by a factor of 2 or more of a computed volume.

For these reasons it is advantageous if the PSF is not determined from a reference measurement, but rather experimentally on the actual sample.

This idea forms the basis for a method for operating a scanning microscope and for determining point spread functions, with which sample images are recorded with the scanning microscope. In such a method it is provided that a sample is scanned with at least one illuminating light beam; that at least one sample image is recorded with a detector device of the scanning microscope during a scan by the illuminating light beam; and that the point spread function, with which a sample image is recorded by the scanning microscope, is computed from the at least one sample image.

A scanning microscope conforming of this type includes a light source device for emitting at least one illuminating light beam, a scanning device for generating a scanning motion of the at least one illuminating light beam across a sample, a detector device for recording at least one sample image during a scan by the illuminating light beam, and electronic control and evaluation means, which are designed to compute a point spread function, with which a sample image is recorded, from the at least one sample image.

In a method known from the prior art, reference objects, such as beads, which are smaller than the microscope resolution, are added to the sample. The PSF with respect to a sample image can be determined from the detector signals with respect to these reference objects. The drawback with this method is that more work is required to prepare the samples.

SUMMARY OF THE INVENTION

A primary object of the invention may be considered to be the provision of a scanning microscope and a method, by means of which it is possible to determine the point spread functions, with which the sample images are recorded with the scanning microscope, without demanding intensive preparation work from a microscope user.

This object is achieved by means of the method exhibiting the features disclosed in the appended method claims and by means of the scanning microscope exhibiting the features disclosed in appended device claims.

Variants of the inventive method and the inventive scanning microscope are the subject matter of the dependent claims and are also explained in greater detail in the following description.

In the method of the aforementioned type, a detector device with receiving elements is used according to the invention, wherein the distance between the detector elements is smaller than a diffraction disk that generates a sample point on the detector device. In accordance with the invention, the detector signals, generated by means of the receiving elements, are in each case read out for different positions of the illuminating light beam on the sample, as a result of which the scanning of the sample allows the detector signals, which are read out, to generate a plurality of sample images. In this case the point spread functions with respect to the different detector signals are defined in each instance by means of an illumination point spread function and a detection point spread function. With respect to all of the detector signals, a matching illumination point spread function is assumed that is shifted in accordance with the scanning motion for different detector signals. In addition, with respect to all of the detector signals, a matching detection point spread function is assumed that takes account of a spatial offset between the detector elements. Furthermore, the plurality of sample images are used to compute the illumination point spread function and the detection point spread function, and these functions are used to compute the point spread functions with respect to the different detector signals.

In the scanning microscope of the aforementioned type, it is provided according to the invention that the detector device has receiving elements, where the distance between the receiving elements is smaller than a diffraction disk that generates a sample point on the detector device; that, in addition, the electronic control and evaluation means are also designed to read out the detector signals, generated by means of the receiving elements, for each of the different positions of the illuminating light beam on the sample, as a result of which the scanning of the sample allows the detector signals, which are read out, to generate a plurality of sample images. In this case the point spread functions with respect to the different detector signals are defined in each instance by means of an illumination point spread function and a detection point spread function. Furthermore, the electronic control and evaluation means are designed to compute the illumination point spread function and the detection point spread function with the plurality of sample images; and these functions are used to compute the point spread functions with respect to the different detector signals, assuming that with respect to all of the detector signals there is a matching illumination point spread function that is shifted in accordance with the scanning motion for different detector signals; and with respect to all of the detector signals there is a matching detection point spread function that takes account of a spatial offset between the detector elements.

The invention is based, in particular, on the recognition that a so-called sub-Airy scanning of the sample generates measured data that allow a precise computation of the PSF. This computation uses knowledge about the PSF during a sub-Airy scan, in particular, the way in which the PSF is obtained from the illumination PSF and the detection PSF. The basic idea is explained in more detail below.

In the case of a simple, non-inventive measurement, with which a single sample image is recorded, the PSF cannot be reliably computed from the recorded image data. Such a computation has too many unknown variables, so that the computation is under-determined.

If a plurality of identical sample images are recorded, nothing changes.

However, additional information that is useful to compute the PSF is obtained, if a plurality of sample images are recorded with different PSFs, and the change in the PSF between the sample images is known. This is precisely what can be achieved with the sub-Airy scan used by the invention.

The principles of sub-Airy scanning go back to Sheppard et al., Optik 80, no. 2, 53 (1982). In the invention detector elements can be used for the sub-Airy scan, wherein the distance between the detector elements is less than 1 Airy. In this case an Airy denotes the size of a diffraction disk that generates a point in the analyzed sample plane on the detector device. For a particular position of the illuminating light beam, several detector elements, in particular, all of the detector elements are read out. For a next position of the illuminating light beam the detector elements are read out again. Such generated detector signals from one and the same detector element are not, for example, added together. Although the detection PSF, which determines the sample area, from which this detector element receives light, is the same for all of the detector signals of this detector element, in this case, however, the illumination PSF changes when the illuminating light beam is guided over the sample. The sample point, from which the observed detector element predominantly receives light, depends on the PSF or the total PSF, which is a product of the illumination PSF and the detection PSF. Therefore, shifting the illumination PSF allows consecutive different sample points to be analyzed with a single detector element. When the scan is completed, each detector element has analyzed a particular sample area. The sequentially recorded detector signals from a detector element may be regarded as a sample image. Therefore, a number of sample images are recorded by means of scanning; and these sample images may correspond to the number of detector elements. The sample areas, which are analyzed by different detector elements, overlap extensively. By computing these sample images it is possible to compute a complete image that has a higher resolution or image quality than the individual sample images.

At this point a central idea of the invention may be seen in the fact that knowledge of the PSF and the change in the PSF is used during a scan.

Therefore, although the PSF is different for each of the sample images, recorded in accordance with the invention, precise information about this difference is available. Therefore, all of the detector signals are based on a matching illumination PSF, with the only difference being a shift in the illumination PSF. This shift is based on the scanning motion of the illuminating light beam. However, the shape and size of the illumination PSF remain unchanged. Since the scanning motion is defined by the actuation of the scanning device, it is known with a high degree of accuracy. Therefore, the shift in the illumination PSF is also known with a high degree of precision.

The detection point spread functions for the sequentially recorded detector signals of the same detector element are identical. For detector signals of different detector elements they differ only in a shift. These shifts are equal to the distances between the different detector elements. The distances may be known or also determined experimentally, as will be described with respect to a later variant.

Thus, a sub-Airy scan provides a plurality of sample images with point spread functions that are determined solely by two unknowns, i.e., exactly one illumination PSF and exactly one detection PSF.

As described, each sample image contains, nevertheless, different information due to the shifts or the offset of the illumination PSF and the detection PSF. Hence, a large number of sample images are recorded with different PSFs without increasing the number of unknown variables. As a result, it is possible to record a sufficient number of sample images so that a computation of the point spread functions of different sample images is over-determined. That means that there is more information available than is absolutely necessary to find a unique solution to the computation of the point spread functions.

At the same time it is advantageous for a user that the amount of effort required does not increase. In principle, just scanning the sample may suffice. During a sub-Airy scan a plurality of sample images is already recorded in any event, so that no additional sample measurements are required to compute the PSFs. Furthermore, no special sample preparation work is required; in particular, no addition of beads of sub-Airy size is necessary.

The aforementioned plurality of sample images is preferably computed to obtain a complete image, so that this complete image has a higher resolution than one of the sample images. In principle, the complete image may be computed as an average of the sample images. Preferably, however, the sample images are used, together with the computation of the point spread functions, to compute a complete image. Thus, the point spread function also flows into the computation of the complete image. In the computation the PSF and the complete image may be two functions to be determined in a common equation. That is, they are computed together.

The above descriptions are mathematically illustrated below for one exemplary embodiment.

According to the invention, n sample images are recorded during a scan. A sample image may comprise, in particular, the detector signals that are recorded one after the one in succession by one and the same detector element. However, in principle, it is also possible to combine the detector signals into sample images in some other way and then to compute a complete image and the PSFs from these sample images.

The signals that are received by the detector elements may be characterized as k=k (s,r). In this case r denotes the scanning position, i.e., the mean position of an illumination spot in the sample plane, and is a vector with values in the three spatial directions x, y, z.

s denotes the shift that is caused by the respective position of a detector element in the plane of the detector device and that is present with respect to the scanning position. Thus, s is also a vector with values in the three spatial directions $s_x$, $s_y$, $s_z$.

There are n different detector elements, which differ in their respective value of s. During a scan operation, r runs through various values, for which the n detector elements record in each instance a signal k.

At this point the detector signal k(s,r) can be described by:

$$k(s,r)=(p \times PSF)(s,r) \qquad \text{formula (1)}$$

where p denotes the sample and indicates the intensity, with which different sample points reflect, when illuminated, the sample light in the direction of the detector device. Depending on the way the measurement is conducted, p may be determined by the reflectivity, the dispersion, the type and density of fluorophores or by other sample properties. For example, p may give the location-dependent density of a fluorophore. The determination of p represents the computation of the complete image.

In the above formula the PSF for the measurement of the value of k(s,r) is denoted by PSF; and x denotes the convolution of p by PSF. According to the above formal [sic: formula], the result of the convolution depends on a function of the variables (s,r). Because p and the point spread functions PSF are linked in a system of equations, the complete image is computed together with the PSF.

The convolution of two functions p and PSF is broadly defined by:

$$(p \times PSF)(r) := \int p(r')PSF(r-r')dr' \qquad \text{formula (2)}$$

The PSF can be represented by a multiplication of an illumination point spread function $PSF_{exc}$ with a detection point spread function $PSF_{det}$.

At this point use is made of the knowledge that the only change in the detection point spread function for different detector elements is a shift that corresponds to the relative position of different detector elements to each other and that is denoted by s:

$$PSF(s,r):=PSF_{exc}(r)PSF_{det}(r+s) \qquad \text{formula (3)}$$

Therefore, the formulas (1) and (2) give:

$$k(s,r)=\int p(r')PSF_{exc}(r-r')PSF_{det}(r+s-r')dr' \qquad \text{formula (3')}$$

Usually the detector elements may be found in one plane, so that for different s values the PSF has no difference in the z direction (see above formula). In general, however, a curved detector surface may also be used, so that a z dependence has to be included. Therefore, the result is that for different detector elements the $PSF_{det}$ is different at the site of the analyzed sample surface or sample plane, where there is a shift $s_x$, $s_y$ and possibly $s_z$, which is different for the detector signals of different detector elements and is the same for the plurality of detector signals from one and the same detector element.

After a read out operation of the measurement signals k to obtain a particular triplet value of r, the position r of the illuminating light beam in the sample plane is changed. Then another set of measurement signals k is recorded and read out.

Upon completion of the scanning operation, the measurement signals are combined into n sample images. The point spread functions with respect to various sample images, with the measured values thereof differing in r and/or s, can be represented by a single PSF, as in the formulas above. In this representation the one PSF is a function of r and s. This is equivalent to a representation by a plurality of PSFs that comprise r and s as the indices or parameters. This can also be referred to as a matrix representation of the PSF.

Thus, the invention refers with a synonymous meaning to exactly one PSF for a plurality of sample images, with this one PSF for these different sample images being different, or to a plurality of different PSFs for different sample images. What is relevant in both cases is that the one PSF or the plurality of PSFs for different sample images has or have only one shift s and one shift r in the illumination PSF, but no other differences for the various sample images.

The above formulas (3), (3') can also be understood as a scan of the illumination point spread function $PSF_{exc}$, using the detection point spread function $PSF_{det}$ at n grid points. The position of the grid points is known from the positions of the detector elements. Because the number of detector elements and, thus, the number of recorded images may be n in size, this corresponds to a large number of grid points. Therefore, an accurate computation of the unknowns in formula (3') is possible. At the same time k is obtained by means of the measurement, and s can be known. As a result, the sample information p and the illumination and detection point spread functions $PSF_{exc}$ and $PSF_{det}$ are unknown and have to be computed.

Formula (1) shows that the larger the difference in the PSF for different (r,s) values, the higher the probability of a more accurate computation is. If the PSF (r,s) values were identical for different (r,s) values, there would just be a repeated measurement that merely provides an improved signal-to-noise ratio, but not a significant gain in information for computing the point spread functions. If, however, the PSFs vary widely for different (r,s) values, then it is possible to obtain n different equations, from each of which the same p and the same illumination and detection point spread functions can be computed.

This computation can be performed iteratively or numerically, in particular, by determining an extremum; that is, by determining a minimum or maximum of a particular function. In the following a representation of a plurality of PSFs is selected, that, instead of the variables (r,s) comprises the parameters r and s, which are combined into a single index in the formula below.

When using multi-frame blind deconvolution, the following function may be selected as the function to be minimized:

$$\sum_{i=1}^{n} \|k_i - p \times PSF_i\|^2 + \sum_{r \neq s}^{n} \|k_r \times PSF_s - k_s \times PSF_r\|^2 \qquad \text{formula (4)}$$

In the case of a non-inventive measurement, the $PSF_i$ values would be independent of each other. That is, there would be n independent point spread functions. As a result, there would not be enough information to unambiguously minimize the above function. Of course, it is also possible to use the additional assumed properties to compute a stable and generally useful solution. However, with the measurement according to the invention very few expressions are unknown, so that the sample p and the illumination and detection point spread functions can be computed precisely and stably.

It is also possible to use an expression that is different from the one in formula (4), in order to determine the aforementioned unknowns from the measured data. The aforementioned multi-frame blind deconvolution is described, for example, by Sroubek et al. in the Journal of Physics, Conference Series 124 (2008). Its use in computing a plurality of photographs of a photographic device is known. In these photographs the point spread functions differ due to random fluctuations in, for example, the air density between the camera and the photographed object, whereas the optical elements of the camera for the plurality of photographs are unchanged and, thus, produce no difference in the point spread functions.

In more general terms, the illumination point spread function and the detection point spread function are preferably computed by iteratively adapting a fit function, wherein the fit function describes a correlation of the recorded sample images to at least the illumination point spread function, to the detection point spread function, to the respective offset between the illumination point spread function and the detection point spread function for the various detector signals, and to a sample function p, which denotes the sample spatially resolved.

The sample function may include a parameter, i.e., a value that is to be determined by the computation, for example, for each x, y, z point of the sample. Thus, the sample function represents the complete image to be determined.

The term "fit function" is defined as a mathematical function that includes parameters having values that, starting from the starting values, are changed in such a way that the fit function is over-determined with the measured data as accurately as possible.

The fit function may include, in particular, an expression, which is to be iteratively adapted and which describes the illumination point spread function, and an expression, which is to be iteratively adapted and which describes the detection point spread function.

These two expressions, which are to be iteratively adapted, may be formed in each case by Zernike polynomials. Zernike polynomials make it easy to determine the aberrations and at the same time the faults in the experimental set-up, for example, a tilting of the cover glass of the sample. In particular, Zernike polynomials can be represented by $Z^m_n (p,\varphi) = R^m_n(p) \cos(m,\varphi)$; and, in particular, the odd Zernike polynomials may be represented by $Z^{-m}_n(p,\varphi) = R^m_n (p) \sin(m,\varphi)$, where m and n are non-negative whole integers; n is greater than or equal to m; $\varphi$ is the azimuthal angle; and p is the normalized radial distance.

The closer the starting values of the parameters, which are to be iteratively determined, are to the values, which are to be determined by the iterative computation, the faster and less prone to error an iterative computation is. Therefore, a theoretical illumination point spread function and a theoretical detection point spread detection, both of which are determined in advance with the given information about the optical imaging means of the scanning microscope, are used preferably as the starting values for the two expressions that are to be iteratively adapted. This determination of the theoretical illumination PSF and the detection PSF may include a simulation or an analytical or iterative computation.

If a theoretical illumination point spread function and a theoretical detection point spread function are determined by means of given information about the optical imaging means of the scanning microscope, then it is possible to determine variances between the theoretical illumination point spread function and the computed illumination point spread function as well between the theoretical detection point spread function and the computed detection point spread function. Aberrations can be identified, based on the variances that are found. For this purpose it is particularly advantageous to represent the illumination PSF and the detection PSF, which are to be computed, by the Zernike polynomials, from which a slightly spherical aberration, coma or astigmatism can be read out, which in turn may indicate errors in the use of the microscope, for example, with respect to the handling of the immersion medium or the cover glass.

The user instructions for handling elements of the scanning microscope, on which the illuminating light or the sample light, emitted by the sample, impinges, may be stored in an electronic memory, where an allocation of the user instructions to various aberrations is also stored. Then the electronic evaluation means can be used to select, as a function of the identified aberrations, the associated user instructions, which are outputted to a user. These instructions may relate, for example, to the orientation of the cover glass or the use of the immersion medium.

There are preferably adaptive optics, with which the aberration of the scanning microscope can be corrected. The adaptive optics may comprise, for example, one or more adjustable mirrors or lenses. In principle, the adaptive optics can be manually operated. Preferably, however, the electronic control and evaluation means are used, as a function of the identified aberrations, to adjust the adaptive optics, in order to reduce aberrations of the scanning microscope.

In principle, the invention can be used to determine the PSF for two dimensions, in particular, for the two lateral directions, which are transverse to the optical axis from the objective lens to the sample, and, thus, to compute the complete image. In this case the complete image can be computed with a resolution or image quality that is better than that obtained with a conventional method, but precise knowledge about the analyzed sample volume is not obtained.

Preferably, therefore, in order to determine the height dependence of the point spread functions, an additional plurality of sample images are recorded, from which at least one additional complete image is computed. In this case the measurements with respect to various complete images differ in the vertical offset between the illumination point spread function and the detection point spread function. Then the plurality of complete images can be used to compute the height dependence of the point spread functions. In this way a significant improvement in determining the height dependence of the point spread functions can be achieved with just two complete images.

Said vertical offset can be achieved, for example, by adjusting a relative height between the focus of the illuminating light and the sample or between the sample and an analyzed plane, which is sharply imaged on the detector device, after recording the sample images for a first complete image. Then the sample is scanned again with at least one illuminating light beam and, in so doing, a plurality of sample images are recorded again and computed to obtain a second complete image. This change in the focus can be effected by adjusting an optical component, on which either the illuminating light or the sample light, but not both the illuminating light and the sample light, impinges.

In a preferred alternative, the sample images for the different complete images are recorded without having to adjust the height of the sample, a light source device, which emits illuminating light, or the detector device. For this purpose the light source device may comprise at least two light source units, which are disposed in planes that are optically conjugate to various sample planes. As an alternative or in addition, the detector device may include for this purpose two detector areas, onto which two different planes are mapped. In the latter case the detector signals, which are recorded by the two detector areas, are different in the vertical offset of their detection PSF. Different cameras or adjacent detector elements of one and the same camera chip may be used as the different detector areas.

In the previous case with two light source units it is possible to alternate between two illumination PSFs, which are distinguished by a vertical offset, but may, otherwise be identical, by using the first or second light source unit. The two light source units may emit one after the other in succession an illuminating light, where in this case the sample images, required for the two complete images, are recorded with one and the same camera of the detector device. However, the light source units can also emit simultaneously the illuminating light beams, if said illuminating light beams can be distinguished, for example, by their polarization or wavelength. As a result, the sample light can also be different and guided, for example, to one specific area of the detector areas, as a function of its polarization or wavelength.

In particular, if two detector areas are used for recording the sample images, on which the two complete images are based, it is advantageous to record the sample images for a first complete image simultaneously with the sample images for a second complete image. This arrangement offers the advantage of speed.

Preference is given to the generation of a multi-color image, which may consist of a plurality of complete images, if for these complete images the sample is scanned with illuminating light of different wavelength ranges, and/or the detector device is used to measure the sample light, coming from the sample and composed of different wavelength ranges. The observable structures of the sample may differ widely, as a function of the wavelength of the light, so that a multi-colored image is associated with a large gain in information. Optimally the illumination PSF and the detection PSF are not highly dependent on the wavelength. Therefore, it is preferred to add to the illumination point spread function to be computed and/or the detection point spread function to be computed a parameter to describe the wavelength dependence of the illumination point spread function and/or the detection point spread function. The value of this parameter can be specified, since the wavelength dependence of optical elements is fairly well known as a rule. As an alternative, a value of the parameter may be determined during the iterative or analytical computation described above.

It is also possible to specify a value for the distance between the detector elements, i.e., the relative positions, of the detector elements to each other. Therefore $\Delta x_i$; $\Delta y_i$ are specified in the formulas listed above. This is advantageous, in order to keep the number of unknown parameters and the number of parameters, which are to be determined, small. As an alternative, however, the fit function that is used may also include parameters, which are to be adapted and which describe the arrangement of the detector elements relative to each other. By determining this arrangement it is possible to determine, in particular, an image magnification, with which a sample plane is mapped onto the detector device, and/or an orientation of the detector device relative to the scanning direction of the illuminating light. These values in turn can be used to compute the complete image or to adjust, in particular, to position, the optical elements of the scanning microscope. The arrangement of the detector elements relative to each other does not have to be specified, since the equations to be solved continue to be over-determined owing to the recording of a relatively large number of sample images, each with a different PSF.

In specifying the functions and/or the starting values of an iterative adjustment of the illumination PSF and the detection PSF it can be used that the illuminating beam path and the detection beam path run for the most part across the same elements. In the case of fluorescence measurements, the major difference lies in the different wavelengths of the illumination light and the sample light. This difference can be used to specify the illumination PSF and the detection PSF.

Preferably it is provided for the sub-Airy scan of the invention that from a read out of the detector elements until a next read out of the detector elements the illuminating light beam is moved in a sample plane by a distance that is smaller than the size of a diffraction disk that a light source point generates in the sample plane. At the same time the illuminating light beam can be moved continuously or step by step with the scanning device.

The light source device for generating the illuminating light beam may comprise one or more light source units, in particular, lasers or LEDs.

In principle, the detector device may be of any type, as long as it can record a sample image in at least one dimension, preferably in two dimensions. In addition, its detector elements have to be arranged so close to each other that the adjacent detector elements exhibit a distance that may be measured between the centers of the adjacent detector elements and that is less than 1 Airy. For this purpose each detector element comprises an optical fiber that transmits the sample light to a photosensitive element, for example, to a pixel of a camera chip or to a photo electron multiplier (photomultiplier, PMT). In principle, each photosensitive element of a camera chip may also represent a detector element without the use of any optical fibers. Furthermore, the detector device may also comprise a plurality of cameras.

The sample light that is to be measured by the detector device is light that is reflected, as a result of the irradiation of the sample with illuminating light, from the sample in the direction of the detector device. The sample light may include, depending on the type of measurement, fluorescent light or other luminescence light or also reflected or scattered illuminating light.

In a preferred variant of the invention the computed point spread functions are used to compute the size of the measuring range, which determines a pixel of the complete image. The said measuring range may be a measurement surface or a measurement volume.

In this case an absolute quantitative evaluation of the complete image is possible in an advantageous way. Hence, it is possible to compute the absolute concentrations of one or more substances in the different measuring ranges by using the computed size of a measuring range. What is required for this purpose as the previously stored information is merely the size of a measurement signal for the number of reference molecules or for the density of the reference molecules of the substance in question. If this reference value is compared with the value of a pixel of the determined complete image, then it is possible to determine the density or the total number of molecules of the substance in question for the measuring range of this pixel.

Compared to conventional methods, in the inventive method the computation of a complete image from a plurality of images can lead to a better image quality or a higher resolution due to the use of information relating to the way, in which the different sample images relate to each other. As a result, the point spread functions, on which the recordings of these sample images are based, can be determined extremely accurately, with which the improved image quality is associated. In addition, a detailed knowledge of the point spread function makes it possible to determine precisely the size of the analyzed sample area.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A method for operating a scanning microscope and for determining point spread functions, with which sample images are recorded with the scanning microscope, comprising
   scanning a sample with at least one illuminating light beam;
   recording at least one sample image with a detector device of the scanning microscope during a scan by said at least one illuminating light beam;
   computing the point spread function, with which a sample image is recorded by the scanning microscope, from the at least one sample image,
   said detector device having receiving elements, where the distance between said receiving elements is smaller than a diffraction disk that generates a sample point on the detector device,
   said receiving elements generating detector signals which are read out for each of the different positions of the illuminating light beam on the sample, as a result of which the scanning of the sample allows the read out detector signals to generate a plurality of sample images, wherein the point spread functions with respect to the different detector signals are defined in each instance by means of an illumination point spread function and a detection point spread function,
   with respect to all of the detector signals, a matching illumination point spread function is shifted in accordance with the scanning motion for different detector signals, and
   with respect to all of the detector signals, a matching detection point spread function takes account of a spatial offset between the detector elements, and
   using the plurality of sample images to compute the illumination point spread function and the detection point spread function, said point spread functions being used to compute the point spread functions with respect to the different detector signals, said sample images are used, together with the computation of the point spread functions, to compute a complete image.

2. The method according to claim 1, wherein the computed point spread functions are used to compute the size of a measuring range, which determines a pixel of the complete image.

3. The method according to claim 1, wherein the illumination point spread function and the detection point spread function are computed by iteratively adapting a fit function, wherein the fit function describes a correlation of the recorded sample images to at least the illumination point spread function, to the detection point spread function, to the respective offset between the illumination point spread function and the detection point spread function for the various detector signals, and to a sample function, which represents the sample spatially resolved.

4. The method according to claim 3, wherein the fit function comprises an expression, which is to be iteratively adapted and which describes the illumination point spread function, and an expression, which is to be iteratively adapted and which describes the detection point spread function.

5. The method according to claim 4, wherein the two expressions, which are to be iteratively adapted, are formed in each case by Zernike polynomials.

6. The method according to claim 4, further comprising using a theoretical illumination point spread function and a theoretical detection point spread detection, both of which are determined in advance with the given information about the optical imaging means of the scanning microscope, as the starting values for the two expressions that are to be iteratively adapted.

7. The method according to claim 1, further comprising determining a theoretical illumination point spread function and a theoretical detection point spread function by means of given information about the optical imaging means of the scanning microscope, determining variances between the theoretical illumination point spread function and the computed illumination point spread function as well between the theoretical detection point spread function and the computed detection point spread function, and identifying aberrations, based on the variances that are found.

8. The method according to claim 7, further comprising
storing user instructions for handling elements of the scanning microscope, on which the illuminating light or the sample light, emitted by the sample, impinges, in an electronic memory,
storing an allocation of the user instructions to various aberrations,
using electronic evaluation means to select, as a function of the identified aberrations, the associated user instructions, which are outputted to a user.

9. The method according to claim 7, wherein the aberrations of the scanning microscope can be corrected with adaptive optics, and using electronic control and evaluation means as a function of the identified aberrations, to adjust the adaptive optics, in order to reduce aberrations of the scanning microscope.

10. The method according to claim 1, further comprising
recording an additional plurality of samples in order to determine the height dependence of the point spread function, from which at least one additional complete image is computed,
wherein the measurements with respect to various complete images differ in the vertical offset between the illumination point spread function and the detection point spread function, and
using the plurality of complete images to compute the height dependence of the point spread functions.

11. The method according to claim 10, further comprising
recording the sample images for the different complete images without having to adjust the height of the sample, a light source device, which emits the illuminating light, or the detector device, for which purpose
the light source device comprises at least two light source units, which are disposed in planes that are optically conjugate to various sample planes, and/or
the detector device comprises two detector areas, onto which two different planes are mapped.

12. The method according to claim 11, further comprising simultaneously recording the sample images for a first complete image with the sample images for a second complete image.

13. The method according to claim 1, wherein each sample is scanned with illuminating light of different wavelength ranges, and/or that the detector device is used to measure the sample light, coming from the sample and composed of different wavelength ranges; and the illumination point spread function to be computed and/or the detection point spread function to be computed includes and/or include a parameter to describe the wavelength dependence of the illumination point spread function and/or the detection point spread function.

14. The method according to claim 3, wherein the fit function includes parameters, which are to be adapted and which describe the arrangement of the detector elements relative to each other, in particular, for determining an image magnification, with which a sample plane is mapped onto the detector device, and/or for determining an orientation of the detector device relative to the scanning direction of the illuminating light.

15. A scanning microscope, comprising
a light source device for emitting at least one illuminating light beam, comprising a scanning device for generating a scanning motion of the at least one illuminating light beam across a sample,
a detector device for recording at least one sample image during a scan by the illuminating light beam,
electronic control and evaluation means, for computing a point spread function, with which a sample image is recorded, from the at least one sample image,
said detector device having receiving elements, where the distance between said receiving elements is smaller than a diffraction disk that generates a sample point on the detector device,
said electronic control and evaluation means further being designed to read out the detector signals, generated by means of the receiving elements, for each of the different positions of the illuminating light beam on the sample, as a result of which the scanning of the sample allows the detector signals, which are read out, to generate a plurality of sample images,
wherein the point spread functions with respect to the different detector signals are defined in each instance by means of an illumination point spread function and a detection point spread function, and
wherein said electronic control and evaluation means are designed to compute an illumination point spread function and a detection point spread function with the plurality of sample images; and these two functions are used to compute the point spread functions with respect to the different detector signals,
and wherein with respect to all of the detector signals, there is a matching illumination point spread function that is shifted in accordance with the scanning motion for different detector signals; and that with respect to all of the detector signals there is a matching detection point spread function that takes account of a spatial offset between the detector elements, said sample images are used, together with the computation of the point spread functions, to compute a complete image.

* * * * *

UNITED STATES PATENT AND TRADEMARK OFFICE
CERTIFICATE OF CORRECTION

PATENT NO. : 10,048,481 B2
APPLICATION NO. : 15/029361
DATED : August 14, 2018
INVENTOR(S) : Ingo Kleppe et al.

It is certified that error appears in the above-identified patent and that said Letters Patent is hereby corrected as shown below:

In the Specification

Column 1, Line 17 now reads: "The present invention relates, in a first aspect to a method" should read --The present invention relates, in a first aspect, to a method--

Column 1, Line 21 now reads: "invention relates to a the structure of the scanning micro-" should read --invention relates to the structure of the scanning micro- --

Column 6, Line 27 now reads: "$PSF(s,r):=PSF_{exe}(r)PSF_{det}(r+s)$ formula (3)" should read --$PSF(s,r):=PSF_{exc}(r)PSF_{det}(r+s)$ formula (3)--

Column 8, Line 26 now reads: "sented by $Z^m_r$, $(p, \varphi)=R^m n(p) \cos(m,\varphi)$; and, in particular, the" should read --sented by $Z^m_n (p,\phi)=R^m_n(p) \cos(m,\phi)$; and, in particular, the--

Column 8, Line 27 now reads: "odd Zernike polynomials may be represented by $Z^{-m}_n(p,\varphi)$" should read --odd Zernike polynomials may be represented by $Z^{-m}_n(p,\phi)$--

Column 8, Line 28 now reads: "$=R^m_n (p) \sin(m,\varphi)$, where m and n are non-negative whole" should read --$=R^m_n (p) \sin(m,\phi)$, where m and n are non-negative whole--

Column 8, Line 29 now reads: "integers; n is greater than or equal to m; $\varphi$ is the azimuthal" should read --integers; n is greater than or equal to m; $\phi$ is the azimuthal--

Column 10, Line 35 now reads: "the detector elements to each other. Therefore $\Delta x$; $\Delta y_i$ are" should read --the detector elements to each other. Therefore $\Delta x$, $\Delta y_l$ are--

Signed and Sealed this
Fourth Day of June, 2019

Andrei Iancu
*Director of the United States Patent and Trademark Office*